United States Patent [19]

Cavalleri et al.

[11] Patent Number: 4,880,789
[45] Date of Patent: Nov. 14, 1989

[54] 2'-SUBSTITUTED-4-DEOXY-THIAZOLO(5,4-C)-RIFAMYCIN SV DERIVATIVES

[75] Inventors: Bruno Cavalleri, Milan; Marco Turconi, Voghera; Giovanni Tamborini, Pogliano Milanese, all of Italy

[73] Assignee: Gruppo Lepetit S.P.A., Gerenzano, Italy

[21] Appl. No.: 238,985

[22] Filed: Aug. 24, 1988

Related U.S. Application Data

[63] Continuation of Ser. No. 945,704, Dec. 23, 1986, abandoned.

[30] Foreign Application Priority Data

Dec. 30, 1985 [GB] United Kingdom ............... 8531887

[51] Int. Cl.$^4$ ............... C07D 513/08; A61K 31/425
[52] U.S. Cl. .................................. 514/183; 540/457; 540/458; 540/459
[58] Field of Search .................. 540/457, 458, 459; 514/183

[56] References Cited

U.S. PATENT DOCUMENTS

| | | | |
|---|---|---|---|
| 4,042,683 | 8/1977 | White et al. ................. | 424/117 |
| 4,116,957 | 9/1978 | Rossetti et al. ............. | 540/457 |
| 4,129,562 | 12/1978 | Cricchio ..................... | 540/458 |
| 4,144,234 | 3/1979 | Cricchio ..................... | 540/458 |
| 4,212,873 | 7/1980 | Cricchio ..................... | 540/458 |

FOREIGN PATENT DOCUMENTS 2084575 4/1982 United Kingdom ............... 540/459

Primary Examiner—Robert T. Bond
Attorney, Agent, or Firm—J. Michael Dixon

[57] ABSTRACT

The present invention concerns new 2'-substituted-4-deoxy-thiazolo[5,4-c]rifamycin SV derivatives having antibacterial activity.

These compounds are compounds obtained by chemical modification of thiazolo[5,4-c]rifamycin SV.

19 Claims, No Drawings

2'-SUBSTITUTED-4-DEOXY-THIAZOLO(5,4-C)-RIFAMYCIN SV DERIVATIVES

CROSS-REFERENCE TO RELATED APPLICATION

This is a continuation of application Ser. No. 945,704, filed Dec. 23, 1986.

The present invention concerns new 2'-substituted-4-deoxy-thiazolo[5,4-c]rifamycin SV derivatives of formula I

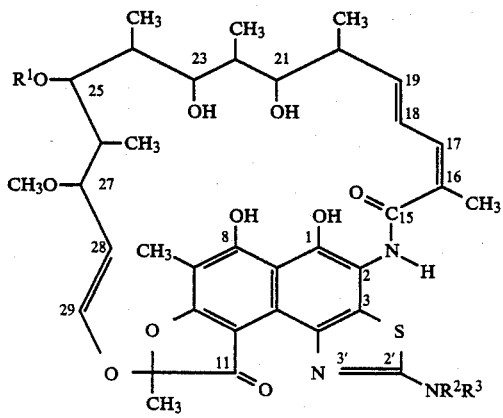

wherein
$R^1$ represents hydrogen or acetyl, $R^2$ and $R^3$ each independently represent $(C_1-C_4)$alkyl or $R^2$ and $R^3$ taken together with the adjacent nitrogen atom represent a 4-7 membered saturated heterocyclic ring which may contain a further hetero group selected from oxygen, sulfur and $-N-R^4$,
$R^4$, $R^4$ represents hydrogen, $(C_1-C_4)$alkyl, hydroxy $(C_2-C_4)$alkyl, $(C_2-C_4)$alkanoyl, $(C_1-C_4)$alkoxycarbonyl, phenyl optionally substituted with 1 to 3 substituents selected from halogeno, hydroxy, $(C_1-C_4)$alkyl and $(C_1-C_4)$alkoxy; phenyl $(C_1-C_4)$alkyl wherein the phenyl ring may be optionally substituted with 1 to 3 substituents selected from halogeno, hydroxy, $(C_1-C_4)$alkyl, and $(C_1-C_4)$alkoxy; phenyl $(C_1-C_4)$alkoxycarbonyl wherein the phenyl ring may be is substituted with from 1 to 3 substituents selected from halogeno, hydroxy, $(C_1-C_4)$alkyl and $(C_1-C_4)$alkoxy, and the pharmaceutically acceptable acid addition salts thereof.

4-deoxy-thiazolo[5,4-c]rifamycin SV (also called "rifamycin P") has been obtained both by fermentation of Nocardia strains and by chemical processes. The fermentation process has been disclosed in GB 1470426 while chemical processes are reported in U.S. Pat. Nos. 4144234 and 4129562.

2'-Alkyl-4-deoxy-thiazolo[5,4-c]rifamycin SV derivatives are described in U.S. Pat. No. 4169839; 2'-hydrazonomethyl 4-deoxythiazolo[5,4-c]rifamycin SV are described in EP-A-5140, while 4-deoxythiazolo[5,4-c]rifamycin SV having a mono-amino substituent or a hydrazino substituent in position 2' are disclosed in DT-A-2741066 and are prepared by reacting 3-bromo rifamycin S with the proper thiourea derivative.

In the present description and claims the term "$(C_1-C_4)$alkyl" either alone or in combination with other groups represents alkyl groups of 1 to 4 carbon atoms such as methyl, ethyl, propyl, 1-methylethyl, 2-methyl-1-propyl 2-methyl-2-propyl and butyl. "$(C_1-C_4)$alkoxy" either alone or in combination with other groups represents alkoxy groups of 1 to 4 carbon atoms such as methoxy, ethoxy, propoxy, 1-methylethoxy, 2-methylpropoxy, 2-methyl-2-propoxy and butoxy. "Halogeno" represents a halogen atom selected from chloro, bromo, iodo, and fluoro. "4–7 membered saturated heterocyclic ring . . . " represents a 4, 5, 6 or 7 membered saturated heterocyclic ring which may contain a further heterogroup selected from oxygen, sulfur, and $-N-R^4$ Preferred examples of said 4–7 membered heterocyclic rings are azetidinyl, pyrrolidinyl, piperidinyl, piperazinyl, oxazolinidinyl, pyrazolidinyl, thiazolidinyl, morpholinyl, imidazolidinyl and the like. A preferred group of compounds of the invention is represented by those compounds of formula I wherein $R^1$ represents acetyl. Another group of preferred compounds is represented by those compounds of formula I wherein $R^2$ and $R^3$ independently represents a $(C_1-C_4)$alkyl group or $R^2$ and $R^3$ taken together with the adjacent nitrogen atom represent a 4–7 membered heterocyclic ring selected from azetidinyl, pyrrolidinyl, piperidinyl, piperazinyl, oxazolinidinyl, pyrazolidinyl, thiazolidinyl, morpholinyl, imidazolidinyl groups and the further ring nitrogen atom when present bears a substituent $R^4$ which is as defined above.

A further preferred group of compounds of the invention includes those compounds of formula I wherein $R^1$ represents acetyl and $R^2$ and $R^3$ independently represent methyl or ethyl, or $R^2$ and $R^3$ taken together with the adjacent nitrogen atom represents a pyrrolidinyl, morpholinyl, piperidinyl or piperazinyl group optionally substituted as defined above with reference to the meanings of $R^4$. Specific preferred embodiments of the invention are represented by the following compounds of formula I:

2'-(4''-morpholinyl) rifamycin P
2'-(1''-piperidinyl) rifamycin P
2'-(4''-methyl-1''-piperazinyl) rifamycin P
2'-(N,N-diethylamino) rifamycin P The compound of the invention are prepared by reacting 4-deoxy-thiazolo[5,4-c]rifamycin SV (i.e. rifamycin P) or 25-desacetyl-4-deoxy-thiazolo[5,4-c]rifamycin SV, i.e. a compound of the following formula II

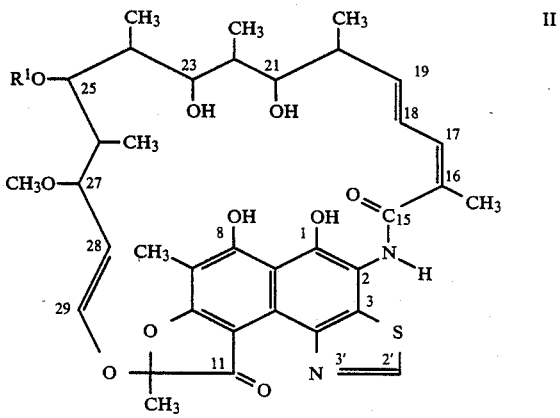

wherein $R^1$ represent hydrogen or acetyl, with an amine of formula $HNR^2R^3$ in the presence of an inert organic solvent, with the proviso that when the $HNR^2R^3$ amine is piperazine $R^4$ is different from hydrogen. To obtain the piperazine derivative wherein $R^4$ is hydrogen, the corresponding phenyl ($C_1$–$C_4$)alkoxycarbonyl derivative is submitted to hydrogenolysis under conditions that prevents the hydrogenation of the ansa double bonds. The reaction temperature is generally between 5° C. and 40° C. and preferably between 15° C. and 30° C. the preferred reaction temperature is room temperature. The inert organic solvents may be one of the organic solvents which do not unfavorably interfere with the reaction course which are capable of at least partially dissolve the starting material of formula II and the amine $HNR^2R^3$ while it is not necessary that either the starting materials or the final products be completely dissolved into the reaction so as to form a homogeneous phase. Representative examples of inert organic solvents are saturated "cyclic" ethers like tetrahydrofuran or dioxane, glycol ethers like dimethoxyethanol and ($C_1$–$C_4$)alkyl alkanoates such as ethyl acetate, propyl acetate, ethylpropionate and the like, and mixtures thereof.

The hydrogenolytic step which is required to obtain the piperazine derivative wherein $R^4$ is hydrogen starting from the corresponding compound wherein $R^4$ is as defined above but different from hydrogen must be carried out under conditions that do not lead to a substantial hydrogenation of the ansa double bonds. This hydrogenolysis is preferably conducted in a polar organic solvent such as a lower alkanol in the presence of a hydrogenation catalyst like palladium on carbon. Most preferred conditions are the presence of absolute ethanol as the solvent and 10% palladium on carbon as the catalyst. The reaction course is monitored as known in the art by HPLC or TLC techniques so that the skilled man is capable of adjusting the specific reaction conditions and deciding when the reaction is to be considered completed.

Usual purification procedures such as extraction with solvents, precipitation by addition of non-solvents, or by changing the pH of the medium, and chromatographic procedures are suitable for the purification of the compounds of the invention Chromatographic procedures include preparative TLC, column chromatography and HPLC.

The physico-chemical data, and purification methods, of some representative compounds of the invention are reported in the following Tables I and II. More particularly, the compounds listed below are compounds of formula I wherein $R^1$ represents acetyl, with the exception of compound 3b wherein $R^1$ represents hydrogen.

TABLE I

| Compound of Example | $R^2$ | $R^3$ | Rifamycin P (g)/solvent (ml) | $HNR^2R^3$ (ml)[1] | Time (h)[1] | Purification[2] | Yield |
|---|---|---|---|---|---|---|---|
| 1a | —$(CH_2)_4$— | | 1/150 THF | 10 | 5 | a,c,f | 18.3 |
| 1b | —$(CH_2)_2O(CH_2)_2$— | | 1/100 THF | 5 | 5 | a,c,e | 20.7 |
| 1c | —$(CH_2)_2N(CH_2)_2$—$C_6H_5$ | | 1/50 EtOAc | 5 + 5 | 2; 18 | a,h,g | 30.5 |
| 1d | —$(CH_2)_2N(CH_2)_2$—$CH_2C_6H_5$ | | 1/50 EtOAc | 5 | 15 | a,c,f | 20.0 |
| 1e | —$(CH_2)_2N(CH_2)_2$—$COOC_2H_5$ | | 0.6/40 EtOAc | 4 | 15 | a,c,f | 34.5 |
| 1f | —$(CH_2)_2N(CH_2)_2$—$COOCH_2$—$C_6H_5$ | | 1.5/100 EtOAc | 2 | 18 | a,c,f | 17.6 |
| 2 | —$(CH_2)_5$— | | 1/— | 15 | 30 | a,c,f | 13.6 |
| 3a | —$(CH_2)_2N(CH_2)_2$—$CH_3$ | | 2/300 EtOAc | 10 + 10 | 1.5; 3.5 | b,c | 57.6 |
| 3b | —$(CH_2)_2N(CH_2)_2$—$CH_3$ 25-desacetyl | | 0.8/100 EtOAc | 4 + 4 | 1.5; 3.5 | b,d,e | 32.8 |
| 3c | —$(CH_2)_2N(CH_2)_2$—$(CH_2)_2OH$ | | 1/50 EtOAc | 5 + 4 | 4; 24 | b,h,f | 17.1 |
| 3d | —$(CH_2)_2N(CH_2)_2$—$C_6H_4Cl$ | | 1/200 EtOAc | 2g | 12 | b,d,f | 30.2 |
| 3e | —$(CH_2)_2N(CH_2)_2$—$C_6H_4OCH_3$p. | | 2/400 EtOAc | 4 | 12 | b,d,f | 9.6 |
| 4 | —$(CH_2)_2N(CH_2)_2$—H | | — | — | — | — | 17.9 |
| 5 | $C_2H_5$ | $C_2H_5$ | 0.5/25 EtOAc | 5 | 120 | — | 6.0 |

Notes to Table I
[1]When two quantities are reported the reagent was added in two portions at the times indicated.
[2](a) Acid treatment as described for compound 1a;
(b) acid/base treatment as described for compound 3a;
(c) preparative TLC, eluent mixture $CH_2Cl_2$/MeOH 95:5, the compound is collected, dissolved with a mixture of EtOAc and acid water, the organic layer is separated, and concentrated to a small volume; the product is precipitated with petroleum ether.
(d) preparative TLC, eluent mixture $CH_2Cl_2$/MeOH 95:5, then worked up as for compound 4;
(e) crystallized from EtOAc;
(f) precipitated from EtOAc with petroleum ether;
(g) precipitated from $CH_2Cl_2$ with petroleum ether;
(h) column chromatography, on Silica Gel 60 (0.06–0.2 mm; Merck Co.) eluent mixture $CH_2Cl_2$/MeOH 95:5.

TABLE II

| Compound of Example | Formula[1] | TLC,Rf[2] | mp, °C. (dec)[3] | MW (LC/MS) | UV[4] (MeOH) $\lambda_{max}$, (nm) | log$^\epsilon$ |
|---|---|---|---|---|---|---|
| 1a | $C_{42}H_{53}N_3O_{11}S$ | 0.36 | 180–184 | 807.8 (M + H $^+$ m/z 808) | 228 | 4.62 |
| | | | | | 308 | 4.46 |
| | | | | | 432 | 4.11 |
| 1b | $C_{42}H_{53}N_3O_{12}S$ | 0.41 | 198–200 | 823.9 | 228 | 4.62 |
| | | | | | 308 | 4.47 |
| | | | | | 432 | 4.08 |
| 1c | $C_{48}H_{58}N_4O_{11}S$ | 0.38 | 179–180 | 899.1 | 230 | sh |
| | | | | | 242 | 4.68 |
| | | | | | 308 | 4.51 |
| | | | | | 430 | 4.08 |
| 1d | $C_{49}H_{60}N_4O_{11}S$ | 0.46 | 171–174 | 913.1 | n.d. | |
| 1e | $C_{45}H_{58}N_4O_{13}S$ | 0.38 | 165–167 | 895.0 (M − H $^+$ m/z 894) | n.d. | |
| 1f | $C_{50}H_{60}N_4O_{11}S$ | 0.75 | 163–166 | 925.1 | 229 | 4.59 |
| | | | | | 310 | 4.44 |
| | | | | | 432 | 3.99 |

TABLE II-continued

| Compound of Example | Formula[1] | TLC,Rf[2] | mp, °C. (dec)[3] | MW (LC/MS) | UV[4] (MeOH) $\lambda_{max}$, (nm) | log$^\epsilon$ |
|---|---|---|---|---|---|---|
| 2 | $C_{43}H_{55}N_3O_{11}S$ | 0.40 | 172–175 | 821.9 | 228 | 4.76 |
|   |   |   |   | (M $-$ m/z 821) | 308 | 4.61 |
|   |   |   |   | (M + H $+$ m/z 822) | 430 | 4.25 |
| 3a | $C_{43}H_{56}N_4O_{11}S$ | 0.57 | 183–185 | 837.0 | 227 | 4.62 |
|   |   |   |   | (M $-$ m/z 837) | 308 | 4.47 |
|   |   |   |   |   | 430 | 4.08 |
| 3b | $C_{41}H_{54}N_4O_{10}S$ | 0.51 | 190–192 | 794.9 | 228 | 4.64 |
|   |   |   |   |   | 308 | 4.50 |
|   |   |   |   |   | 432 | 4.12 |
| 3c | $C_{44}H_{58}N_4O_{12}S$ | 0.53 | 183–185 | 867.0 | 227 | 4.61 |
|   |   |   |   |   | 308 | 4.46 |
|   |   |   |   |   | 430 | 4.07 |
| 3d | $C_{48}H_{57}ClN_4O_{11}S$ | 0.39 | 182–183 | 933.5 | 228 | 4.67 |
|   |   |   |   |   | 252 | 4.72 |
|   |   |   |   |   | 307 | 4.54 |
|   |   |   |   |   | 431 | 4.11 |
| 3e | $C_{49}H_{60}N_4O_{12}S$ | 0.41 | 176–179 | 929.1 | 237 | sh |
|   |   |   |   |   | 242 | 4.69 |
|   |   |   |   |   | 309 | 4.51 |
|   |   |   |   |   | 432 | 4.08 |
| 4 | $C_{42}H_{54}N_4O_{11}S$ | 0.30 | 200–201 | 822.9 | 230 | 4.55 |
|   |   |   |   |   | 312 | 4.41 |
|   |   |   |   |   | 436 | 3.97 |
| 5 | $C_{42}H_{55}N_3O_{11}S$ | 0.39 | 180–183 | 809.9 | 228 | 4.61 |
|   |   |   |   |   | 307 | 4.46 |
|   |   |   |   |   | 429 | 4.12 |

Notes to Table II
On Silica Gel 60 $F_{254}$ plates (Merck); solvent-run 10.0 cm.
[1]The analytical results for C, H, N, S (and Cl) were within ± 0.4% of the teoretical values.
[2]Eluent mixture $CHCl_3$/MeOH 9/1. Under these conditions the $R_f$ of rifamycin P is 0.42.
[3]Determined in glass capillary tubes.
[4]Rifamycin P shows the following values of $\lambda_{max}$ in methanol nm: 225, 260, 305, 352, 412.
n.d. = not determined.

The compounds of the invention possess antimicrobial activity against gram positive and some gram negative bacteria and are also active against Mycobacteria strains, in particular against *Mycobacterium tuberculosis*.

The minimum inhibitory concentration (MIC) of representative compounds of the invention was determined using two-fold dilution method in microtiter system. The media used were: Todd-Hewitt broth (Difco) for steptococci; Iso-Sensitest broth (Oxoid) for staphylococci and gram-negative bacteria. The final inoculum was about $10^4$ cfµ/ml. MIC was read as the lowest concentration which showed no visible growth after 18–24 hours incubation at 37° C. For M. tuberculosis $H_{37}R_V$ the inoculum consisted of 0.5–1% of a 7–9 day culture in Dubos medium. The tests were carried out in Kirschner medium supplemented with 10% horse serum. Observations were made after 7-days incubation at 37° C.

The results obtained are summarized in the following Table III:

TABLE III

In vitro antibacterial acitvity (MIC, mg/l)

| Organism | 1a | 2 | 1b | 1c | 1d | 1e | 1f |
|---|---|---|---|---|---|---|---|
| Staphylococcus aureus ATCC 6538 | 0.016 | 0.003 | 0.001 | 0.004 | 0.004 | 0.032 | 0.064 |
| S. aureus TOUR L 165 | 0.004 | 0.006 | 0.002 | 0.008 | 0.008 | 0.064 | 0.064 |
| S. aureus TOUR$^a$ L 165 | 0.016 | 0.2 | 0.008 | 0.016 | 0.016 | 0.064 | 0.064 |
| S. aureus TOUR$^b$ L 1282 | >128 | >100 | 64 | >128 | >128 | 128 | >128 |
| Streptococcus pyogenes C203 | 0.008 | 0.05 | 0.032 | 0.032 | 0.064 | 0.064 | 0.125 |
| S. faecalis ATCC 7080 | 2 | 1.6 | 1 | 1 | 1 | 4 | 2 |
| S. faecalis ATCC 10541 | n.t. | n.t. | n.t. | n.t. | n.t. | n.t. | n.t. |
| S. pneumoniae UC 41 | 0.032 | 0.05 | 0.016 | 0.004 | 0.064 | 0.064 | 0.064 |
| Proteus vulgaris XI9H ATCC 881 | 16 | 6.25 | 8 | 16 | 32 | 16 | 64 |
| Escherichia coli SKF 12140 | 16 | 12.5 | 16 | 4 | 32 | 16 | >128 |
| Klebsiella pneumoniae ISM | 32 | 25 | 32 | >128 | 64 | 32 | >128 |
| Pseudomonas aeruginosa ATCC 10145 | 8 | 6.25 | 16 | 8 | 16 | 32 | 32 |
| Mycobacterium tuberculosis H37RV ATCC 9360 | 2 | 0.2 | 2 | 1 | 0.125 | 2 | 0.5 |

| Organism | 3a | 3b | 3c | 3d | 3e | 4 | 5 |
|---|---|---|---|---|---|---|---|
| Staphylococcus aureus ATCC 6538 | 0.001 | 0.008 | 0.008 | 0.064 | 0.064 | 0.125 | 0.032 |
| S. aureus TOUR L 165 | 0.004 | 0.008 | 0.016 | 0.064 | 0.064 | 0.125 | 0.064 |
| S. aureus TOUR$^a$ L 165 | 0.004 | 0.016 | 0.032 | 0.25 | 0.5 | 0.125 | 0.5 |
| S. aureus TOUR$^b$ L 1282 | 32 | >128 | 64 | >128 | >128 | >128 | >128 |
| Streptococcus pyogenes C203 | 0.032 | 0.063 | 0.016 | 0.064 | 0.125 | 0.125 | 0.064 |
| S. faecalis ATCC 7080 | 2 | 1 | 4 | 2 | 4 | 2 | 1 |
| S. faecalis ATCC 10541 | n.t. | n.t. | n.t. | n.t. | n.t. | n.t. | n.t. |
| S. pneumoniae UC 41 | 0.032 | 0.063 | 0.008 | 0.125 | 0.064 | 0.064 | 0.032 |
| Proteus vulgaris XI9H ATCC 881 | 8 | 8 | 16 | >128 | 64 | 8 | 32 |
| Escherichia coli SKF 12140 | 16 | 8 | 8 | 1 | 8 | 8 | 32 |

TABLE III-continued

| In vitro antibacterial acitvity (MIC, mg/l) | | | | | | | |
|---|---|---|---|---|---|---|---|
| *Klebsiella pneumoniae* ISM | 32 | 16 | 32 | >128 | >128 | 16 | 64 |
| *Pseudomonas aeruginosa* ATCC 10145 | 16 | 8 | 128 | 128 | 8 | 16 | |
| *Mycobacterium tuberculosis* H37RV ATCC 9360 | 1 | 1 | 4 | 1 | 0.25 | n.t. | 0.5 |

[a] Supplemented with 30% bovine serum
[b] Rifampicin resistant strain
[c] not tested The antimicrobial activity of the compounds of the invention is also confirmed in "in vivo" tests. The results of experimental septicemia in mice are reported in the following Table IV.

The animals (groups of five mice) were infected by intraperitoneal injection of 16-hour broth culture of *S. aureus* tour L 165. Inocula were adjusted so that untreated animals died of septicemia within 48 hours. Animals were treated once daily for three days starting immediately after infection. On the 10th day the value for the ED$_{50}$ in mg/kg/day was calculated by the method of SPEARMAN-KÄRBER (Finney, D. J., Statistical method in biological assay, page 524. C. Griffin Ltd., London, 1952), on the basis of the percentage of surviving animals at each dose.

TABLE IV

| Compound of Example | ED$_{50}$ (mg/Kg/day) | |
|---|---|---|
| | os | sc |
| 1b | 0.21 | 0.21 |
| 1c | 2.5 | 0.63 |
| 3a | 0.36 | 0.16 |
| 3b | 13 | 10 |
| 3c | >20 | 3.3 |
| 3d | 3.3 | 3.3 |
| 3e | 1.9 | 0.63 |
| 5 | 0.82 | 0.21 |
| 2 | 0.63 | 0.16 |

The following examples further illustrate the invention.

EXAMPLE 1

(a) 2'-(1"-PyrrolidinyL) rifamycin P

Pyrrolidine (10 ml) is added to a solution of 1.0 g (1.35 mmole) of rifamycin P in 150 ml of THF at room temperature. The reaction mixture is stirred for 5 hours then it is poured into ice-water, acidified with diluted hydrochloric acid and extracted with ethyl acetate (EtOAc) (2×100 ml). The combined extracts are washed with water to neutrality, dried on anhydrous sodium sulphate and concentrated to a small volume at 45° C. under vacuum. The addition of petroleum ether gives a precipitate that was collected and purified by preparative TLC as follows: the solid is dissolved in few milliliter of MeOH and the solution is applied to Silica Gel plates 60 PF$_{254}$ (merck) that are developed with a mixture of CH$_2$Cl$_2$/MeOH 95:5. The zone corrsponding to the title product is scraped off and eluted with methanol (MeOH). The extract is evaporated to dryness, the residue is dissolved in ethyl acetate and washed with diluted hydrochloric acid, dried on sodium sulphate and concentrated to a small volume. By adding petroleum ether a precipitate forms which is filtered off and dried under vacuum.

The yield and the physico-chemical date are reported in Tables I and II.

By following the procedure of the above Example (1a) and using the appropriate amine reactant the following compounds are obtained whose reaction conditions, purification details, yields and physicochemical data are reported in Tables I and II:

(b) 2'-(4"-morpholinyl) rifamycin P

HNR$^2$R$^3$=morpholine (c) 2'(4"-phenyl-1"-piperazinyl) rifamycin P

HNR$^2$R$^3$=1-phenylpiperazine (d) 2'(4"-phenylmethyl-1"-piperazinyl) rifamycin P HNR$^2$R$^3$=1-phenylpiperazine (e) 2'(4"-ethoxycarbonyl-1"-piperazinyl) rifamycin P HNR$^2$R$^3$=1-ethoxycarbonylpiperazine (f) 2'(4"-phenylmethoxycarbonyl-1"-piperazinyl) rifamycin P HNR$^2$R$^3$=1-phenylmethoxycarbonylpiperazine

EXAMPLE 2

2'-(1"-Piperidinyl) rifamycin P

Rifamycin P (1.0 g, 1.35 mmole) is dissolved in 15 ml of piperidine and the resulting solution is stirred for 30 hours at room temperature. The reaction mixture is poured in ice-water and worked up as described in the foregoing Example (1a). Purification details, yield and physico-chemical data are reported in Tables I and II.

EXAMPLE 3

(a) 2'-(4"-Methyl-1"-piperazinyl) rifamycin P

1-Methylpiperazine (10 ml) is added to a solution of rifamycin P (2.0 g, 2.7 mmol) in 300 ml of EtOAc and the reaction mixture is stirred for 90 min at room temperature, then an additional 10 ml of 1-methylpiperazine is added. Stirring is continued for 3.5 hours, then the reaction mixture is poured into ice-water and made acidic is with diluted hydrochloric acid, maintaining the pH between 4 and 5.

The organic layer is discarded and the aqueous phase is brought to about pH 7 with NaHCO$_3$ and extracted with EtOAc. The organic extract is dried over sodium sulfate and concentrated to a small volume. By cooling the compound of the title is obtained as crystalline powder which precipitates. Purification details, yield and physico-chemical data are reported in Tables I and II.

By following the procedure of the above Example (3a) and using the appropriate amine reactant the following compounds are obtained whose purification details, yield and physico-chemical data are reported in Tables I and II.

(b) 25-Desacetyl-2'-(4"-methyl-1-piperazinyl) rifamycin P (starting from 25-desacetyl rifamycin P)

HNR$^2$R$^3$=1-methylpiperzine (c) 2'-[4"(2'''-hydroxyethyl)-1"-piperazinyl]rifamycin P $HNR^2R^3$ = 1-(2-hydroxyethyl)piperazine (d) 2'-[4"(4'''-chlorophenyl)-1-piperazinyl]rifamycin P $HNR^2R^3$ = 1-(4-chlorophenyl)piperazine (e) 2'-[4"(4'''-methoxyphenyl)-1-piperazinyl]rifamycin P, $HNR^2R^3$ = 1-(4-methoxyphenyl)-piperazine.

EXAMPLE B 4

2'-(1"-Piperazinyl) rifamycin P

A solution of 0.22 g (0.23 mmole) of 2'-[4"-phenylmethoxycarbonyl-1"-piperazinyl]rifamycin P in 40 ml of absolute ethanol is left under hydrogen stream with stirring at room temperature and atmospheric pressure in the presence of 50 mg of 10% palladium on carbon for 1 hour. The reaction is monitored by TLC (Rf 0.4, relative to the starting compound). Once the reaction is complete the reaction mixture is filtered and the solvent evaporated. The residue is dissolved with MeOH and purified by preparative TLC on Silica Gel 60 $PF_{254}$ plates (eluent mixture $CHCl_3$/MeOH 9:1). The zones which contain the product of the title are eluted with MeOH. The methanolic extracts are evaporated to dryness, the residue is dissolved with ethyl acetate and the solution is washed with an aqueous $NaHCO_3$ solution at pH 8.5, dried over sodium sulfate and concentrated to a small volume. Upon adding petroleum ether the compounds of the title precipitates which is filtered off and dried under vacuum.

EXAMPLE 5

2'-(N,N-dimethylamino) rifamycin P

N,N-Diethylamine (5 ml) is added to a solution of rifamycin P (0.5 g, 0.67 mmole) in 25 ml of EtOAc and the reaction mixture is allowed to stand at room temperature for five days, then it is poured into ice-water and made acid with diluted hydrochloric acid. The organic layer is separated, washed with water to neutrality, dried on sodium sulphate and evaporated to dryness. The residue is dissolved with 2 ml of $CH_2Cl_2$ and subjected to flash chromatography by applying it to a column of 35 g of Silica Gel 60 (0.04–0.06 mm) Merck which is developed with:

(a) $CH_2Cl_2$ (250 ml), (b) $CH_2Cl_2$ containing 0.5% (v/v) of methanol (500 ml), (c) $CH_2Cl_2$ containing 1% (v/v) of methanol (500 ml), (d) $CH_2Cl_2$ containing 1.8% (v/v) of methanol (1 liter).

This last mixture elutes the product of the title and is collected in fractions of 100 ml each (12 fractions). Those fractions which contains the product of the title are combined and evaporated to dryness obtaining 33 mg of pure compound.

Preparation of the starting materials:

rifamycin P (4-deoxy-thiazolo[5,4-c]rifamycin SV rifamycin P is prepared as described in GB patent No. 1470426, U.S. Pat. No. 4144234 or U.S. Pat. No. 4129562.

2'-Methoxycarbonyl rifamycin P

2'-Methoxycarbonyl rifamycin P is prepared as described by Cricchio et al., in Tetrahedron, 36, 1415–1421 (1981) and U.S. Pat. No. 4129562.

25-Desacetyl rifamycin P

A solution of 4.5 g (5.5 mmole) of 2'-methoxycarbonyl rifamycin P in 200 ml of acetone and 100 ml of 50% aqueous NaOH is allowed to stand at room temperature with stirring. The reaction is monitored by TLC ($CHCl_3$/MeOH, 95:5) until the starting compound disappears (about 30 min). The reaction mixture was poured into ice-water and extracted with EtOAc. The extracts are dried on sodium sulfate and then evaporated to dryness under vacuum during 30 min. The residue is dissolved into 300 ml of the same acetone-/aqueous NaOH mixture and the solution is evaporated again. The residue is dissolved with $CHCl_3$ and purified by silica gel (220 g) column chromatography eluting with $CHCl_3$ containing increasing amounts of MeOH (from 1.5 to 2% in volume). Fractions containing the desired product are pooled, and the solvents are evaporated to dryness. By crystallization from EtOAc, 3.5 g (90%) of the desired compound is obtained; mp 172°–174° C.;

UV(MeOH) $\lambda_{max}$ nm (log ε) 224 (4.26), 260 (4.21) 298 (4.17), 405 (4.14).

Anal. Calcd for $C_{36}H_{44}N_2O_{10}S$: C 62.05. H 6.36; N 4.02; S 4.60.

Found: C 61.76; H 6.30; N 3.95; S 4.47.

We claim:

1. A compound of the formula:

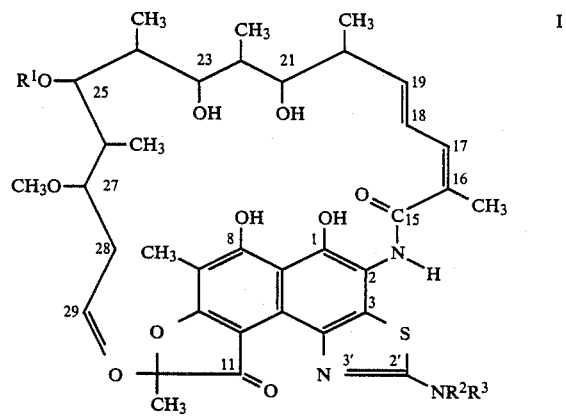

wherein $R^1$ represents hydrogen or acetyl, $R^2$ and $R^3$ each independently represent ($C_1$-$C_4$)alkyl or $R^2$ and $R^3$ taken together with the adjacent nitrogen atom represent a 4–7 membered saturated heterocyclic ring which may contain a further hetero group selected from oxygen, sulfur and —N—$R^4$, wherein said heterocyclic ring is selected from the group consisting of azetidinyl, pyrrolidinyl, piperidinyl, piperazinyl, oxazolinidinyl, pyrazolindinyl, thiazolidinyl, morpholinyl, imidazolidinyl and the further ring nitrogen atom when present bears a substituent $R^4$, wherein said $R^4$ is selected from the group consisting of hydrogen, ($C_1$-$C_4$)alkyl, hydroxy ($C_2$-$C_4$)alkyl, ($C_2$-$C_4$)alkanoyl, ($C_1$-$C_4$)alkoxycarbonyl, phenyl optionally substituted with 1 to 3 substituents selected from halogeno, hydroxy, ($C_1$-$C_4$)alkyl and ($C_1$-$C_4$)alkoxy; phenyl ($C_1$-$C_4$)alkyl wherein the phenyl ring may be optionally substituted with 1 to 3 substituents selected from halogeno, hydroxy, ($C_1$-$C_4$)alkyl, and ($C_1$-$C_4$)alkoxy; phenyl ($C_1$-$C_4$)alkoxycarbonyl wherein the phenyl ring may be optionally substituted from 1 to 3 substituents selected from halogeno, hydroxy, ($C_1$-$C_4$)alkyl and ($C_1$-$C_4$)alkoxy, and the pharmaceutically acceptable acid addition salts thereof.

2. A compound of claim 1 wherein $R^1$ represents acetyl.

3. A compound of claim 1 which is selected from
2'-(4"-morpholinyl) rifamycin P
2'-(1"-piperidinyl) rifamycin P
2'-(4"-methyl-1"-piperazinyl) rifamycin P, and
2'-(N,N-diethylamino) rifamycin P.

4. A process for preparing a compound of claim 1 which comprises reacting a compound of the formula:

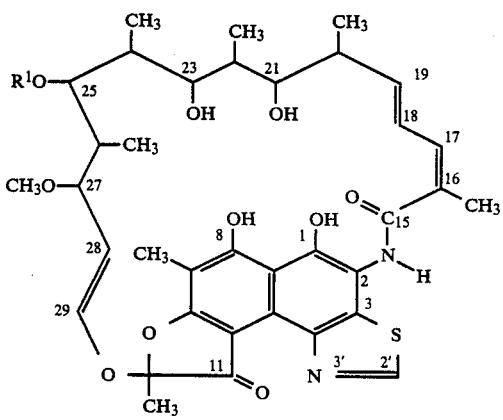

wherein $R^1$ represents hydrogen or acetyl,
(a) with an amine of formula $HNR^2R^3$ in the presence of an inert organic solvent, to obtain a compound of claim 1 wherein the $NR^2R^3$ group is defined in claim 1 with the provision that $NR^2R^3$ does not represent an unsubstituted piperazine;
(b) when a compound of claim 1 is desired wherein the $NR^2NR^3$ group is represented by an unsubstituted piperazine, subjecting to controlled hydrogenolysis the corresponding compound of claim 1 wherein $R^4$ represent phenyl($C_1$-$C_4$)alkoxycarbonyl.

5. A process as claimed in claim 4 wherein the reaction temperature of step (a) is between 5° and 40° C.

6. A process as claimed in claim 4 wherein the reaction temperature of step (a) is room temperature.

7. A process as claimed in claim 4 wherein the hydrogenolysis of step (b) is carried out in a polar organic solvent in the presence of a hydrogenation catalyst.

8. A antibacterial composition which comprises a compound of claim 1 present in a quantity sufficient to exhibit antibacterial activity in admixture with a pharmaceutically acceptable carrier.

9. A method for treating bacterial infections comprising administering to a patient in need thereof, a compound according to claim 1 in a quantity sufficient to exhibit antibacterial activity.

10. A compound according to claim 1 wherein $R^2$ and $R^3$ are each independently represented by a $C_{1-4}$ alkyl.

11. A compound according to claim 1 wherein $R^2$ and $R^3$ are each represented by ethyl.

12. A compound according to claim1 wherein said $R^2$ and $R^3$ taken together with the adjacent nitrogen atom represent a 4–7 membered saturated heterocyclic ring which may contain a further hetero group selected from oxygen, sulfur and —N—$R^4$, wherein said heterocyclic ring is selected from the group consisting of azetidinyl, pyrrolidinyl, piperidinyl, piperazinyl, oxazolinidinyl, pyrazolindinyl, thiazolidinyl, morpholinyl, imidazolidinyl and the further ring nitrogen atom when present bears a substituent $R^4$, wherein said $R^4$ is selected from the group consisting of hydrogen, ($C_1$-$C_4$)alkyl, hydroxy ($C_2$-$C_4$)alkyl, ($C_2$-$C_4$)alkanoyl, ($C_1$-$C_4$)alkoxycarbonyl, phenyl optionally substituted with 1 to 3 substituents selected from halogeno, hydroxy, ($C_1$-$C_4$)alkyl and ($C_1$-$C_4$)alkoxy; phenyl ($C_1$-$C_4$)alkyl wherein the phenyl ring may be optionally substituted with 1 to 3 substituents selected from halogeno, hydroxy, ($C_1$-$C_4$)alkyl, and ($C_1$-$C_4$)alkoxy; phenyl ($C_1$-$C_4$)alkoxy-carbonyl wherein the phenyl ring may be is substituted with from 1 to 3 substituents selected from halogen, hydroxy, ($C_1$-$C_4$)alkyl and ($C_1$-$C_4$)alkoxy, and the pharmaceutically acceptable acid addition salts thereof.

13. A compound according to claim 1 wherein $R^2$ and $R^3$ taken together with the adjacent nitrogen atom represent a pyrrolidinyl, morpholinyl, piperidinyl or piperazinyl group optionally substituted with $R^4$ wherein $R^4$ is as defined in claim 1.

14. A pharmaceutical composition according to claim 12 wherein $R^2$ and $R^3$ are each independently represented by a $C_{1-4}$ alkyl.

15. A pharmaceutical composition according to claim 14 where $R^2$ and $R^3$ are each represented by ethyl.

16. A pharmaceutical composition according claim 12 wherein $R^2$ and $R^3$ taken together with the adjacent nitrogen atom represent a 4–7 membered saturated heterocyclic ring which may contain a further hetero group selected from oxigen, sulfur and —N—$R^4$, wherein said heterocyclic ring is selected from the group consisting of azetidinyl, pyrrolidinyl, piperidinyl, piperazinyl, oxazolinidinyl, pyrazolindinyl, thiazolidinyl, morpholinyl, imidazolidinyl and the further ring nitrogen atom when present bears a substituent $R^4$, wherein said $R^4$ is selected from the group consisting of hydrogen, ($C_1$-$C_4$)alkyl, hydroxy ($C_2$-$C_4$)alkyl, ($C_2$-$C_4$)alkanoyl, ($C_1$-$C_4$)alkoxycarbonyl, phenyl optionally substituted with 1 to 3 substituents selected from halogeno, hydroxy, ($C_1$-$C_4$)alkyl and ($C_1$-$C_4$)alkoxy; phenyl ($C_1$-$C_4$)alkyl wherein the phenyl ring may be optionally substituted with 1 to 3 substituents selected from halogeno, hydroxy, ($C_1$-$C_4$)alkyl, and ($C_1$-$C_4$)alkoxy; phenyl ($C_1$-$C_4$)alkoxy-carbonyl wherein the phenyl ring may be optionally substituted with from 1 to 3 substituents selected from halogeno, hydroxy, ($C_1$-$C_4$)alkyl and ($C_1$-$C_4$)alkoxy, and the pharmaceutically acceptable acid addition salts thereof.

17. A method according to claim 9 wherein $R^2$ and $R^3$ are each independently represented by a $C_{1-4}$ alkyl.

18. A method according to claim 17 wherein $R^2$ and $R^3$ are each represented by ethyl.

19. A method according to claim 9 wherein $R^2$ and $R^3$ together with the adjacent nitrogen atom represent a 4–7 membered saturated heterocyclic ring which may contain a further hetero group selected from oxygen, sulfur and —N—$R^4$, wherein said heterocyclic ring is selected from the group consisting of azetidinyl, pyrrolidinyl, piperidinyl, piperazinyl, oxazolinidinyl, pyrazolindinyl, thiazolidinyl, morpholinyl, imidazolidinyl and the further ring nitrogen atom when present bears a substituted R$^4$, wherein said R$^4$ is selected from the group consisting of hydrogen, (C$_1$-C$_4$)alkyl, hydroxy (C$_2$-C$_4$)alkyl, (C$_2$-C$_4$)alkanoyl, (C$_1$-C$_4$)alkoxycarbonyl, phenyl optionally substituted with 1 to 3 substituents selected from halogeno, hydroxy, (C$_1$-C$_4$)alkyl and (C$_1$-C$_4$)alkoxy; phenyl (C$_1$-C$_4$)alkyl wherein the phenyl ring may be optionally substituted with 1 to 3 substituents selected from halogeno, hydroxy, (C$_1$-C$_4$)alkyl, and (C$_1$-C$_4$)alkoxy; phenyl (C$_1$-C$_4$)alkoxy-carbonyl wherein the phenyl ring may be is substituted with from 1 to 3 substituents selected from halogeno, hydroxy, (C$_1$-C$_4$)alkyl and (C$_1$-C$_4$)alkoxy, and the pharmaceutically acceptable acid addition salts thereof.

* * * * *

UNITED STATES PATENT AND TRADEMARK OFFICE
CERTIFICATE OF CORRECTION

PATENT NO. : 4,880,789

DATED : November 14, 1989

INVENTOR(S) : Bruno Cavalleri, et al.

It is certified that error appears in the above-identified patent and that said Letters Patent is hereby corrected as shown below:

Col. 1, line 37, reads "$R^4$, $R^4$ represents" and should read --$R^4$ represents--

Col. 8, line 24, reads "1-phenylpiperazine" and should read --1-benzylpiperazine--

Col. 9, line 36, reads "dimethylamino" and should read --diethylamino--

Col. 13, line 1, reads "substituted" and should read --substituent--

Signed and Sealed this

Ninth Day of April, 1991

*Attest:*

HARRY F. MANBECK, JR.

*Attesting Officer*   *Commissioner of Patents and Trademarks*